US009458043B2

(12) United States Patent
Simon

(10) Patent No.: US 9,458,043 B2
(45) Date of Patent: Oct. 4, 2016

(54) UTILIZATION OF WALL THICKNESS MEASUREMENT IN COMBINATION WITH THERMAL IMAGING OF CONTAINERS

(71) Applicant: Emhart Glass S.A., Cham (CH)

(72) Inventor: Jonathan S. Simon, Pleasant Valley, CT (US)

(73) Assignee: Emhart Glass S.A., Cham (CH)

( * ) Notice: Subject to any disclaimer, the term of this patent is extended or adjusted under 35 U.S.C. 154(b) by 558 days.

(21) Appl. No.: 14/081,330

(22) Filed: Nov. 15, 2013

(65) Prior Publication Data

US 2015/0142163 A1   May 21, 2015

(51) Int. Cl.
| | |
|---|---|
| G06F 19/00 | (2011.01) |
| C03B 9/41 | (2006.01) |
| G01N 33/38 | (2006.01) |
| G01J 5/00 | (2006.01) |
| G01N 21/90 | (2006.01) |

(52) U.S. Cl.
CPC .............. C03B 9/41 (2013.01); G01N 21/90 (2013.01); G01N 33/386 (2013.01); *G01J 2005/0048* (2013.01); *G01J 2005/0077* (2013.01); *G01N 2021/9063* (2013.01); *G05B 2219/2635* (2013.01); *Y02P 40/57* (2015.11)

(58) Field of Classification Search
CPC ....... C03B 27/06; C03B 27/062; C03B 9/41; G01N 21/90; G01N 33/386; G01N 2021/9063; G01J 2005/0048; G01J 2005/0077; G05B 2219/2635; Y02P 40/57
See application file for complete search history.

(56) References Cited

U.S. PATENT DOCUMENTS

| | | | | |
|---|---|---|---|---|
| 1,843,160 A | * | 2/1932 | Ingle | ................. C03B 9/16 65/203 |
| 3,535,522 A | * | 10/1970 | Green | ................. G01B 11/06 250/352 |
| 5,164,676 A | * | 11/1992 | Baker | ................. G01B 7/28 324/662 |
| 8,462,203 B2 | | 6/2013 | Holtkamp et al. | |
| 8,782,390 B2 | * | 7/2014 | Haaf | ................. G06F 9/4403 710/8 |
| 2003/0155281 A1 | * | 8/2003 | Welker | ................. G01N 21/90 209/524 |
| 2006/0096319 A1 | * | 5/2006 | Dalstra | ................. G01J 5/0003 65/29.11 |
| 2010/0147029 A1 | * | 6/2010 | Ishigame | ................. C03B 9/385 65/82 |
| 2001/0141265 | | 6/2011 | Holtkamp et al. | |

(Continued)

FOREIGN PATENT DOCUMENTS

EP   2 336 740   6/2011

OTHER PUBLICATIONS

Del Nobile, M. A., et al. "Design of plastic bottles for packaging of virgin olive oil." Journal of Food Science—Chicago—68.1 (2003): 170-175.*

(Continued)

*Primary Examiner* — Michael D Masinick

(74) *Attorney, Agent, or Firm* — Reinhart Boerner Van Deuren s.c.

(57) ABSTRACT

A closed loop temperature and wall thickness-based control system for improving process yield and quality while reducing dependence on operator skill utilizes intensity information from a hot end container imaging system and wall thickness information from a hot glass container wall thickness measurement system. By utilizing both the container intensity information and the measured wall thickness information it is possible to provide separate feedback signals responsive to temperature variations and thickness variations. These signals are used to implement automatic closed loop control of the I.S. machine.

23 Claims, 3 Drawing Sheets

(56) References Cited

U.S. PATENT DOCUMENTS

| | | | |
|---|---|---|---|
| 2011/0141264 A1* | 6/2011 | Holtkamp | C03B 9/41 348/86 |
| 2011/0141265 A1* | 6/2011 | Holtkamp | G01J 5/0003 348/86 |
| 2012/0261850 A1* | 10/2012 | Simon | B29C 49/4823 264/40.6 |
| 2015/0127134 A1* | 5/2015 | Simon | G05B 19/042 700/158 |
| 2015/0142163 A1* | 5/2015 | Simon | C03B 9/41 700/158 |

OTHER PUBLICATIONS

Yue, Qin, et al. "Ultralow density, hollow silica foams produced through interfacial reaction and their exceptional properties for environmental and energy applications." Journal of Materials Chemistry 21.32 (2011): 12041-12046.*

* cited by examiner

UTILIZATION OF WALL THICKNESS MEASUREMENT IN COMBINATION WITH THERMAL IMAGING OF CONTAINERS

BACKGROUND OF THE INVENTION

Field of the Invention

The present invention relates generally to the operation of an I.S. machine and more particularly to improving process yield and quality while reducing dependence on operator skill by utilizing feedback information from a hot end container imaging system to implement automatic closed loop control of the I.S. machine.

A system and method for monitoring hot glass containers at the hot end as they stream from an I.S. machine manufacturing them is disclosed in European Patent Application Publication No. EP 2 336 740 A1, to Holtkamp et al., entitled "Method and System for Monitoring and Controlling a Glass Container Forming Process," in U.S. Pat. No. 8,462,203, to Holtkamp et al., entitled "Method and System for Monitoring and Controlling a Glass Container Forming Process," and in U.S. Patent Application Publication No. US 2011 0141265 A1, to Holtkamp et al., entitled "System and Method for Monitoring Hot Glass Containers to Enhance Their Quality and Control the Forming Process," all three of which are assigned to the assignee of the present patent application, and all three of which are hereby incorporated herein by reference in their entirety.

While these systems and methods enable the quality of hot glass containers manufactured by an I.S. machine to be monitored, it would be beneficial to use the large amount of information available on the characteristics of the hot glass containers provided by these systems and methods to further enhance the quality of the hot glass containers being manufactured by the I.S. machine. In this regard, it would be beneficial to use some of the information regarding the characteristics of the hot glass containers provided by these hot glass imaging systems and methods to provide improved feedback information that is then utilized to implement automatic closed loop control of the IS machine, thereby leading to improved process yield and quality of the hot glass containers being produced while reducing dependence on operator.

However, the use of the output signals of a thermal camera providing intensity information characteristic of both temperature and wall thickness can be problematic, inasmuch as a corrective action for an incorrect wall thickness in hot glass containers may not result in a corrective action for an incorrect hot glass container temperature.

It will thus be appreciated that it would be desirable to provide a system and method to improve process yield and quality while reducing dependence on operator skill by providing and utilizing additional sensed information about the hot glass containers that can improve the accuracy of corrective actions based upon information from a hot end container imaging system implemented as an automatic closed loop control of the I.S. machine.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

The disadvantages and limitations of the background art discussed above are overcome by the present invention. With this invention, a closed loop temperature and wall thickness-based control system and method improve process yield and quality while reducing dependence on operator skill by utilizing feedback information from a hot end container imaging system to implement automatic closed loop control of the I.S. machine.

The proposed invention combines the imaging system sensitive to infrared wavelengths referenced above with an on-line, hot glass container wall thickness measurement system. With the additional information provided by the wall thickness sensor, it is possible for the closed loop temperature and wall thickness-based control system and method of the present invention to provide separate feedback signals responsive to temperature variations and thickness variations.

In a system embodiment, a system for enhancing process yield and quality of containers produced by an I.S. machine includes: a thermal imaging measurement device adapted to generate intensity output signals representative of the intensity of the thermal radiation from hot glass containers after their formation in the I.S. machine as the hot glass containers pass the thermal imaging measurement device; a wall thickness measurement device adapted to generate wall thickness output signals representative of the wall thickness of the hot glass containers after their formation in the I.S. machine as the hot glass containers pass the wall thickness measurement device; a signal processing module adapted to receive the intensity output signals from the thermal imaging measurement device and the wall thickness output signals from the wall thickness measurement device and in response thereto to generate estimated temperature signals representative of the temperatures of the hot glass containers after their formation in the I.S. machine; and a control system adapted to receive the wall thickness output signals and the estimated temperature signals and in response thereto to provide modified signals to operate the I.S. machine to produce glass containers having desired characteristics.

In another system embodiment, a system for enhancing process yield and quality of containers produced by an I.S. machine includes: a thermal camera that is sensitive to radiation in the near infrared ("NIR") region and is adapted to generate intensity output signals representative of the intensity of thermal radiation emitted from hot glass containers after their formation in the I.S. machine as the hot glass containers pass the thermal imaging measurement device, wherein the intensity output signals include contributions from both the temperature of the hot glass containers and the wall thickness of the hot glass containers; an optical wall thickness measurement device adapted to generate wall thickness output signals representative of the wall thickness of the hot glass containers after their formation in the I.S. machine as the hot glass containers pass the wall thickness measurement device; a signal processing module adapted to receive the intensity output signals from the thermal imaging measurement device and the wall thickness output signals from the wall thickness measurement device and in response thereto to generate estimated temperature signals substantially representative of only the temperatures of the hot glass containers after their formation in the I.S. machine; and an I.S. machine control system adapted to receive predefined parameters, the wall thickness output signals, and the estimated temperature signals, and in response thereto to provide modified event timing signals to operate the I.S. machine, and in response to the predefined parameters and in the absence of the wall thickness output signals and the estimated temperature signals, to provide unmodified event timing signals to operate the I.S. machine.

In still another system embodiment, a system for enhancing process yield and quality of containers produced by an I.S. machine includes: a thermal imaging measurement device adapted to generate intensity output signals representative of the intensity of the thermal radiation from hot glass containers; a wall thickness measurement device adapted to generate wall thickness output signals representative of the wall thickness of the hot glass containers; a signal processing module adapted to receive the intensity output signals and the wall thickness output signals and in response thereto to generate estimated temperature signals representative of the temperatures of the hot glass containers; and a control system adapted to receive the wall thickness output signals and the estimated temperature signals and in response thereto to provide event timing signals to operate the I.S. machine.

In a method embodiment, the process yield and quality of containers produced by an I.S. machine are enhanced by steps including: generating intensity output signals representative of the intensity of the thermal radiation from hot glass containers after their formation in the I.S. machine; generating wall thickness output signals representative of the wall thickness of the hot glass containers after their formation in the I.S. machine; generating estimated temperature signals representative of the temperatures of the hot glass containers after their formation in the I.S. machine in response to the intensity output signals and the wall thickness output signals; and a control system adapted to receive the wall thickness output signals and the estimated temperature signals and in response thereto to provide event timing signals to operate the I.S. machine.

The closed loop temperature and wall thickness-based control system and method to improve process yield and quality while reducing dependence on operator skill by providing and utilizing sensed wall thickness information derived from the hot glass containers to improve the accuracy of corrective actions based upon information from a hot end container imaging system implemented as an automatic closed loop control of the I.S. machine. Finally, the closed loop temperature and wall thickness-based control system and method of the present invention achieves numerous advantages without incurring any substantial relative disadvantage.

DESCRIPTION OF THE DRAWINGS

These and other advantages of the present invention are best understood with reference to the drawings, in which.

DETAILED DESCRIPTION OF AN EXEMPLARY EMBODIMENT

Figure 1:
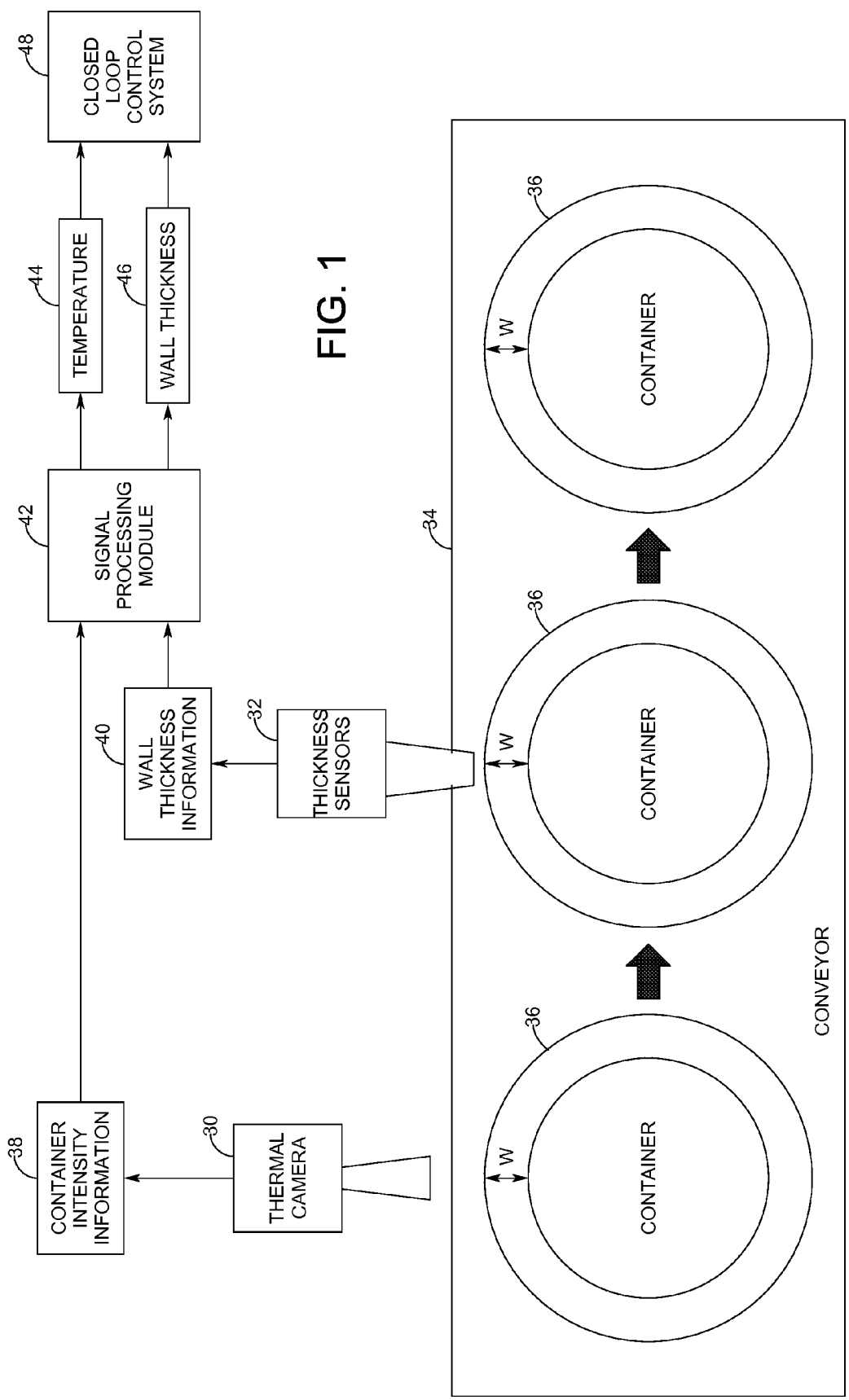
FIG. 1 is a schematic depiction of an overview of the closed loop temperature and wall thickness-based control system of the present invention showing hot glass containers on a conveyor being monitored by a thermal camera and a thickness sensor.

An exemplary overview of the closed loop temperature and wall thickness-based control system of the present invention is shown in FIG. 1. A thermal camera 30 and a hot glass thickness measuring probe 32 are located along a conveyor 34 which transports hot glass containers 36 (each having a wall thickness W) from an I.S. Machine (not shown). The thermal camera 30 is a thermal imaging measurement device that is sensitive to radiation in the near infrared ("NIR") region, and as such it can detect NIR radiation emitted from the hot glass containers 36. The thermal camera 30 generates container thermal intensity information 38, which are intensity output signals that are representative of the intensity of the thermal radiation from the hot glass containers 36 which pass the thermal camera 30 on the conveyor 34 immediately after their formation in an I.S. machine, which include contributions from both the temperature of the hot glass containers 36 and the wall thickness of the hot glass containers 36.

Similarly, the hot glass thickness measuring probe 32 generates wall thickness information 40 that are signals representative of the wall thickness of the hot glass containers 36 which pass the hot glass thickness measuring probe 32 on the conveyor 34 after their formation in an I.S. machine. The hot glass thickness measuring probe 32 may be, for example, an optical wall thickness sensor capable of measuring wall thickness in hot glass containers such as their optical sensors sold by Precitec, Inc. of Wixom, Mich., under their trademark CHRocodile. In this way, container thermal intensity information 38 and the wall thickness information 40 are collected from the passing hot glass containers 36 by the thermal camera 30 and the hot glass thickness measuring probe 32, respectively. By properly aligning the container thermal intensity information 38 and the wall thickness information 40 in time (with the timing and number of container passages), the container thermal intensity information 38 and the wall thickness information 40 for the same hot glass container 36 can be compared.

Figure 2:
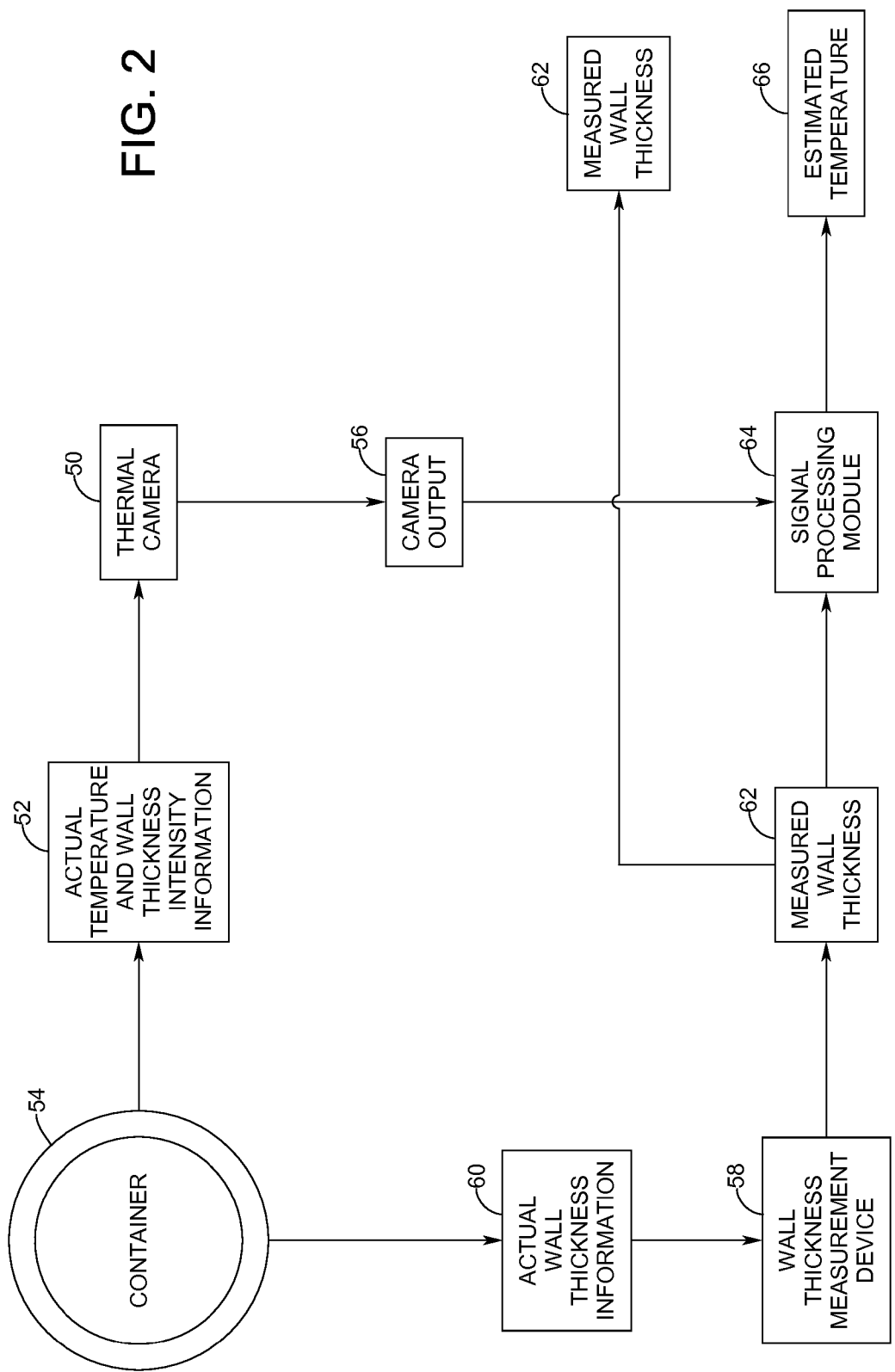
FIG. 2 is a schematic block diagram showing an approximate physical model approach for modeling the signal processing module of the system of FIG. 1.
Figure 3:
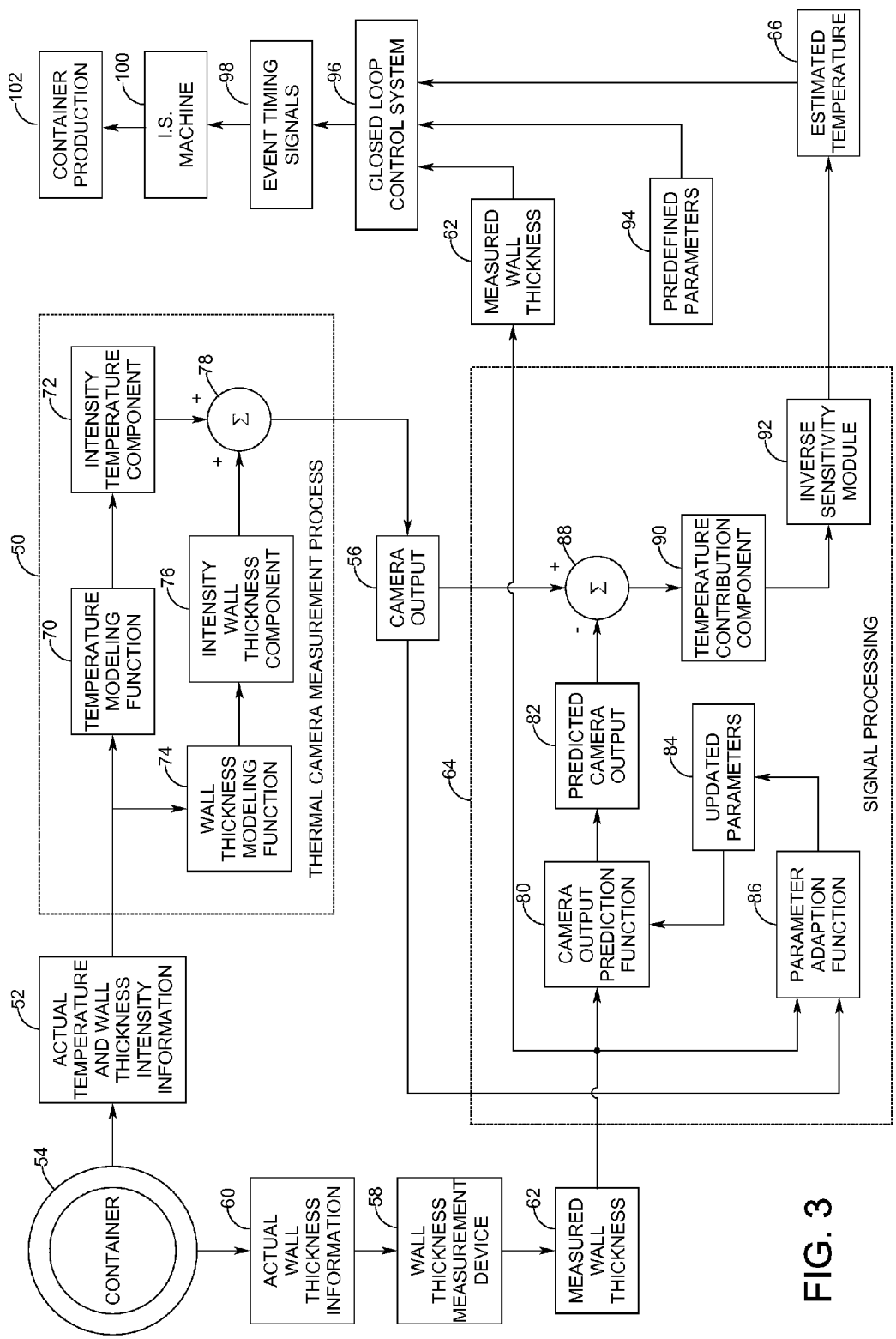
FIG. 3 is a detailed schematic block diagram showing exemplary signal processing using an empirical temperature estimation approach for the signal processing module of the system of FIG. 1 and the use of the signals generated by the system to provide a closed loop control system.

As will be detailed with respect to FIGS. 2 and 3, various methodologies make it possible to utilize the measured values for thickness and intensity to estimate the glass temperature. The necessary alignment of the container thermal intensity information 38 and the wall thickness information 40 are accomplished with a signal processing block 42 that also performs a temperature estimation and which will provide as outputs temperature values 44 and wall thickness values 46. The temperature values 44 are calculated values of the glass temperature of the hot glass containers 54 and the wall thickness values 46 are values of the wall thickness of the hot glass containers 54 that were obtained by the hot glass thickness measuring probe 32 and the wall thickness information 40.

These temperature values 44 and wall thickness values 46 may then be routed to a closed loop control system 48, which will provide appropriate corrective action to modify the predefined parameters that control the I.S. machine in its production of containers in order to achieve and maintain desired values for the temperature values 44 and the wall thickness values 46.

Two possible specific implementations will be described below with reference to FIGS. 2 and 3, respectively. In the approximate physical model approach of FIG. 2, an approximate mathematical model of the underlying physical process is utilized. In the exemplary signal processing schematic diagram of FIG. 3, an empirical regression approach is utilized.

Approximate Physical Model Approach

The photon flux leaving the surface of a hot body at temperature T and a given wavelength, λ, is given (see Ernest O. Doeblin, *Measurement Systems Application and Design*, pg. 555-561, McGraw Hill Book Company 1975) by:

$$N_\lambda = \frac{\varepsilon_\lambda 2\pi c}{\lambda^4 (e^{c_2/\lambda T} - 1)} \quad \text{Equation 1}$$

Where $N_\lambda$=hemispherical spectral photon flux, C=the speed of light, $C_2=14,388 \times 10^{-6}$ m-K, and $\epsilon_\lambda$=emissivity at given wavelength.

For a detector, which is sensitive within the wavelength range $\lambda_1$ to $\lambda_2$ the output intensity signal, I, will be found by integrating Equation 1 over the range of frequencies to obtain:

$$I = C_3 \int_{\lambda_1}^{\lambda_2} N_\lambda d\lambda \quad \text{Equation 2}$$

Where $C_3$ is a constant related to the specific geometry, optics, and sensitivity of the detector.

It may be seen from Equations 1 and 2 that the output of the detector will be related (i.e., sensitive to) the temperature of the body being measured.

The difficulty with utilizing such a measurement system for hot glass containers, is that the emissivity factor, $\epsilon_\lambda$, in Equation 1, is also dependent upon the thickness of the glass.

Following the approach in Ircon Application Note AN109, (http://www.yumpu.com/en/document/view/6641976/glass-temperature-measurement-ircon), the relationship between the emissivity factor, $\epsilon_\lambda$, and wall thickness is derived as follows:

First from Kirchoff's Law:

$$\epsilon_\lambda = 1 - t_\lambda - r_\lambda \quad \text{Equation 3}$$

where $t_\lambda$=transmittance, and $r_\lambda$=reflectance.

While for glass at wavelengths less than 7 microns (which is the range of interest) the reflectance is small and relatively constant, the transmittance depends upon both the wavelength and the thickness, x, of the glass.

In particular we have:

$$t_\lambda = e^{-k_\lambda x} \quad \text{Equation 4}$$

where $k_\lambda$=spectral absorption coefficient. The spectral absorption coefficient is a measurable, physical property that depends upon the glass composition, but also upon the wavelength and the temperature of the glass.

Combining Equation 1-4 gives:

$$I = C_3 \int_{\lambda_1}^{\lambda_2} \frac{(1 - e^{-k_\lambda x} - r_\lambda) 2\pi c}{\lambda^4 (e^{c_2/\lambda T} - 1)} d\lambda \quad \text{Equation 5}$$

which relates the measured detector output, I, to the wall thickness, x, and the temperature, T.

The key concept of the closed loop temperature and wall thickness-based control system of the present invention is that given the measured detector output (the container thermal intensity information 38), I, and the measured wall thickness (the wall thickness information 40), x, from the wall thickness measurement, Equation 5 may be solved (possibly numerically) for the unknown glass Temperature T.

It is noted that the above relationship is only approximate, with notable approximations, including the assumption of a uniform wall temperature, and neglecting any radiation received from the opposite side of the hot glass container 36. It is however assumed that the approximation is adequate to provide an estimate of the glass temperature (the temperature value 44) that is adequate for providing improved process control.

The approach just described is illustrated schematically in FIG. 2. A thermal camera 50 receives thermal actual temperature and wall thickness intensity information 52 from a hot glass container 54, and produces a camera output signal 56 which is representative of the intensity of the thermal radiation that the thermal camera 50 has received.

A wall thickness measurement device 58 transforms (through a physical measurement process) actual wall thickness information 60 to a measured wall thickness signal 62. A signal processing module 64 (which is a Numerical Equation Solver) receives the actual temperature and wall thickness intensity information 52 and the measured wall thickness signal 62 and iteratively obtains a value for the unknown glass temperature, T that satisfies Equation 5. The resulting solution is then output as an estimated temperature signal 66.

Empirical Regression Approach

The approaches taken by the closed loop temperature and wall thickness-based control system of the present invention for the thermal camera 30 and the signal processing block 42 of FIG. 1 will now be discussed, prior to a discussion of the implementation of these approaches in FIG. 3. In this example the measured values $x_m$ of the wall thickness and the measured values $I_m$ of the intensity will initially be used to build an empirical regression model that will predict the wall thickness as function of measured intensity.

Specifically, for N sets of measured values, some functional dependence may be assumed to be given by:

$$\begin{aligned} I_m[1] &\quad f(x_m[1], p) + g(T[1]) \\ I_m[2] &\quad f(x_m[2], p) + g(T[2]) \\ I_m[3] &= f(x_m[3], p) + g(T[3]) \\ &\vdots \\ I_m[N] &\quad f(x_m[N], p) + g(T[N]) \end{aligned} \quad \text{Equation 6}$$

where f=a function of the current measured wall thickness, a vector of unknown parameters p, $I_m[k]$=the kth measured value of intensity, $X_m[k]$=the kth measured value of wall thickness, and $g(T[k])$=the kth contribution to the output due to the temperature of the glass.

Further, $g(T[k])$ may be viewed as an error $e[k]$ that is incurred if it is assumed that the output was entirely due to the thickness variation. Through an optimization procedure, a set of parameters p to minimize the magnitude of the error $e[k]$ can be determined. In other words, the portion of the output that is due to the thickness variation is accounted for, and the remaining error may then be assumed to be due to the contribution of the temperature.

The portion of the output due to the temperature variation is solved as:

$$T[k] = g^{-1}(I_m[k] - f(x_m[k, p])) \quad \text{Equation 7}$$

where $g^{-1}$=the inverse of function $g(T)$.

It should be noted that it may be assumed that the function g(T) is known, either through analytical means or through an empirical calibration where only the temperature of the glass is varied.

Of particular interest, due to its simplicity and readily available techniques for minimizing the error, is the typical linear regression approach where an Mth order polynomial function which may be fitted is of the form:

$$f(x_m[k],p) = p_0 + p_1 x_m[k] + p_2 x^2_m[k] + \ldots p_M x^M_m[k] \quad \text{Equation 8}$$

In this case, a Recursive Least Square algorithm (see William L Brogan, *Modern Control Theory*, pg. 92, Prentice-Hall, Inc. 1982) may be utilized to provide an online update of the coefficient values. So long as the production conditions are relatively steady, the updating may be turned off once a stable set of values has been obtained. Other techniques such as the use of a forgetting factor, which exponentially decreases the importance of the older data points, may be utilized to account for slow variations in the coefficients.

The approach just described is illustrated schematically in FIG. 3. The exemplary thermal camera measurement process that shall be assumed to be taking place internally within the thermal camera 50 is shown in detail. Further, the signal processing process that may be utilized in the signal processing module 64 to provide the estimated temperature signal 66 is presented in detail.

The assumed model of the thermal camera measurement process represented in the thermal camera 50 models how the overall intensity camera output signal 56 provided as an output by the thermal camera 50 represents a combination of a contribution from the actual temperature of the glass in the hot glass container 54 as well as a contribution from the actual wall thickness of the hot glass container 54. Specifically, a temperature modeling function 70 implementing the function g(T) operates on the actual temperature and wall thickness intensity information 52 to produce an intensity temperature component 72 that is the component of the overall intensity due to the glass temperature variation, and a wall thickness modeling function 74 implementing the function f(x) operates on the actual temperature and wall thickness intensity information 52 to produce an intensity wall thickness component 76 that is the component of the overall intensity due to wall thickness variations. The intensity temperature component 72 and the intensity wall thickness component 76 are then added together by a summer 78 to produce the camera output signal 56.

The signal processing module 64 operates on the measured wall thickness signal 62 and the camera output signal 56 to compute the estimated temperature signal 66 as follows. The signal processing module 64 receives the measured wall thickness signal 62 from the wall thickness measurement device 58. A camera output prediction function 80 then calculates a predicted camera output 82 for the portion of the measured wall thickness signal 62 that is due to wall thickness by implementing the function $f_a(x,p)$ operating on the measured wall thickness signal 62 and using updated parameter values 84 $p$ provided by a parameter adaption function 86 to optimize the accuracy of the predicted camera output 82.

The predicted camera output 82 is subtracted from the camera output signal 56 by a summer 88, thereby producing a temperature contribution component 90 that is the portion of the measured wall thickness signal 62 that is due to temperature. If the parameter adaption function 86 is enabled, then updated parameter values 84 are calculated using the measured wall thickness signal 62 and the camera output signal 56, with the parameter adaption function 86 providing the best fit between the measured wall thickness signal 62 and the camera output signal 56. The temperature contribution component 90 may be interpreted as the portion of the camera output signal 56 that is not dependent upon the wall thickness, in other words, the portion due to the temperature sensitivity. With this interpretation, an inverse sensitivity function 92 $g^{-1}(v)$ may be used to compute the estimated temperature signal 66.

Thus, it will be appreciated that the measured wall thickness signal 62 and the estimated temperature signal 66 have been provided by the closed loop temperature and wall thickness-based control system of the present invention. These signals will be used to modify defined parameters 94 that are used by a closed loop control system 96 to provide modified event timing signals 98 to operate an I.S. machine 100, which modified event timing signals 98 result in container production 102 (including the hot glass containers 54) which have desired characteristics. Without the measured wall thickness signal 62 and the estimated temperature signal 66, unmodified event timing signals 98 operating the I.S. machine 100 will be controlled solely by the predefined parameters 94 provided to the event timing signals 98. By also providing the measured wall thickness signal 62 and the estimated temperature signal 66 to the closed loop control system 96, the closed loop control system 96 will produce the event timing signals 98 that are enhanced to improve container process yield and quality.

By way of example and without limiting the applicability of the measured wall thickness signal 62, it may be used in the closed loop control system 96 to automatically adjust the event timing signals 98 to influence how the parison stretches in the blow mold, which will affect vertical glass distribution in the blown container and will thereby affect the wall thickness. This may, for example, be done by the closed loop control system 96 adjusting the event timing signals 98 to vary one or more of: 1. the timing of the start of final blow (the amount of time the parison has to stretch in the blow mold prior to being blown); 2. the blank mold temperature which may be adjusted by varying the cooling of the blank mold (which influences the temperature of the parison skin and how long it will take to reheat and stretch in the blow mold); and 3. the duration that the glass of a parison remains in contact with the blank mold (which again influences the temperature of the parison skin and how long it will take to reheat and stretch in the blow mold).

Also by way of example and without limiting the applicability of the estimated temperature signal 66, it may be used in the closed loop control system 96 to automatically adjust the event timing signals 98 to influence heat removal from the container. This may, for example, be done by the closed loop control system 96 adjusting the event timing signals 98 to vary one or more of: 1. the amount of time that the glass of a parison remains in contact with the blow mold; 2. the amount of time that the final blow air is supplied (when the final blow air is supplied it influences the heat removal both in that it pushes the glass of the blown container against the inner walls of the blow mold, increasing the thermal contact conductance, and it increases the internal heat removal through convection since it carries away heat from the inside of the blown container with the exhausted blow air); and 3. the temperature of the blow mold, which may be adjusted by varying the cooling of the blow mold.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A system for enhancing process yield and quality of containers produced by an I.S. machine, comprising:
   a thermal imaging measurement device adapted to generate intensity output signals representative of the intensity of the thermal radiation from hot glass containers after their formation in the I.S. machine as the hot glass containers pass the thermal imaging measurement device;
   a wall thickness measurement device adapted to generate wall thickness output signals representative of the wall thickness of the hot glass containers after their formation in the I.S. machine as the hot glass containers pass the wall thickness measurement device;
   a signal processing module adapted to receive the intensity output signals from the thermal imaging measurement device and the wall thickness output signals from the wall thickness measurement device and in response thereto to generate estimated temperature signals representative of the temperatures of the hot glass containers after their formation in the I.S. machine; and
   a control system adapted to receive the wall thickness output signals and the estimated temperature signals and in response thereto to provide modified signals to operate the I.S. machine to produce glass containers having desired characteristics.

2. A system as defined in claim 1, wherein the thermal imaging measurement device comprises:
   a thermal camera that is sensitive to radiation in the near infrared ("NIR") region and detects NIR radiation emitted from the hot glass containers.

3. A system as defined in claim 1, wherein the intensity output signals include contributions from both the temperature of the hot glass containers and the wall thickness of the hot glass containers.

4. A system as defined in claim 1, wherein the wall thickness measurement device is an optical sensor capable of measuring wall thickness in hot glass containers.

5. A system as defined in claim 1, wherein the signal processing module comprises:
   a camera output prediction module adapted to calculate a predicted camera output for the portion of the intensity of the thermal radiation from hot glass containers that is due to wall thickness based upon the wall thickness output signals.

6. A system as defined in claim 5, wherein the signal processing module additionally comprises:
   a summer adapted to subtract the predicted camera output from the camera output signal to thereby produce a temperature contribution component that is the portion of the intensity of the thermal radiation from hot glass containers that is due to temperature.

7. A system as defined in claim 6, wherein the signal processing module additionally comprises:
   an inverse sensitivity module adapted to calculate the estimated temperature signals based upon the temperature contribution component from the summer.

8. A system as defined in claim 5, wherein the signal processing module additionally comprises:
   a parameter adaption module adapted to receive the camera output signals and the wall thickness output signals and in response thereto to provide updated parameter values to the camera output prediction module to optimize the accuracy of the predicted camera output.

9. A system as defined in claim 1, wherein the control system is further adapted to receive predefined parameters and in response thereto to provide unmodified signals to operate the I.S. machine in the absence of the wall thickness output signals and the estimated temperature signals, and to provide the modified signals to operate the I.S. machine in response to the predefined parameters, the wall thickness output signals, and the estimated temperature signals.

10. A system as defined in claim 1, wherein the signal processing module generates the estimated temperature signals by iteratively solving the equation $$I = C_3 \int_{\lambda_1}^{\lambda_2} \frac{(1 - e^{-k_\lambda x} - r_\lambda) 2\pi c}{\lambda^4 (e^{c_2/\lambda T} - 1)} d\lambda$$

wherein I is the intensity output signal from the thermal imaging measurement device, x is the wall thickness output signal, and T the estimated temperature signal.

11. A system for enhancing process yield and quality of containers produced by an I.S. machine, comprising:
   a thermal camera that is sensitive to radiation in the near infrared ("NIR") region and is adapted to generate intensity output signals representative of the intensity of thermal radiation emitted from hot glass containers after their formation in the I.S. machine as the hot glass containers pass the thermal imaging measurement device, wherein the intensity output signals include contributions from both the temperature of the hot glass containers and the wall thickness of the hot glass containers;
   an optical wall thickness measurement device adapted to generate wall thickness output signals representative of the wall thickness of the hot glass containers after their formation in the I.S. machine as the hot glass containers pass the wall thickness measurement device;
   a signal processing module adapted to receive the intensity output signals from the thermal imaging measurement device and the wall thickness output signals from the wall thickness measurement device and in response thereto to generate estimated temperature signals substantially representative of only the temperatures of the hot glass containers after their formation in the I.S. machine; and an I.S. machine control system adapted to receive predefined parameters, the wall thickness output signals, and the estimated temperature signals, and in response thereto to provide modified event timing signals to operate the I.S. machine, and in response to the predefined parameters and in the absence of the wall thickness output signals and the estimated temperature signals, to provide unmodified event timing signals to operate the I.S. machine.

12. A system for enhancing process yield and quality of containers produced by an I.S. machine, comprising:
a thermal imaging measurement device adapted to generate intensity output signals representative of the intensity of the thermal radiation from hot glass containers;
a wall thickness measurement device adapted to generate wall thickness output signals representative of the wall thickness of the hot glass containers;
a signal processing module adapted to receive the intensity output signals and the wall thickness output signals and in response thereto to generate estimated temperature signals representative of the temperatures of the hot glass containers; and
a control system adapted to receive the wall thickness output signals and the estimated temperature signals and in response thereto to provide event timing signals to operate the I.S. machine.

13. A method for enhancing process yield and quality of containers produced by an I.S. machine, comprising:
generating intensity output signals representative of the intensity of the thermal radiation from hot glass containers after their formation in the I.S. machine;
generating wall thickness output signals representative of the wall thickness of the hot glass containers after their formation in the I.S. machine;
generating estimated temperature signals representative of the temperatures of the hot glass containers after their formation in the I.S. machine in response to the intensity output signals and the wall thickness output signals; and
providing modified signals in response to the wall thickness output signals and the estimated temperature signals to operate the I.S. machine to produce glass containers having desired characteristics.

14. A method as defined in claim 13, wherein the generating wall thickness output signals step is performed by a thermal imaging measurement device as the hot glass containers pass the thermal imaging measurement device.

15. A method as defined in claim 13, wherein the thermal radiation from hot glass containers is in the near infrared ("NIR") region.

16. A method as defined in claim 13, wherein the intensity output signals include contributions from both the temperature of the hot glass containers and the wall thickness of the hot glass containers.

17. A method as defined in claim 13, wherein the generating wall thickness output signals step is performed by a wall thickness measurement device as the hot glass containers pass the wall thickness measurement device.

18. A method as defined in claim 13, wherein the generating estimated temperature signals step comprises:
calculating a predicted camera output for the portion of the intensity of the thermal radiation from hot glass containers that is due to wall thickness based upon the wall thickness output signals.

19. A system as defined in claim 18, wherein the generating estimated temperature signals step comprises:
subtracting the predicted camera output from the camera output signal to thereby produce a temperature contribution component that is the portion of the intensity of the thermal radiation from hot glass containers that is due to temperature.

20. A method as defined in claim 19, wherein the generating estimated temperature signals step comprises:
calculating the estimated temperature signals based upon the temperature contribution component from the summer.

21. A method as defined in claim 18, wherein the generating estimated temperature signals step comprises:
providing updated parameter values to optimize the accuracy of the predicted camera output in response to the camera output signals and the wall thickness output signals.

22. A method as defined in claim 13, wherein the providing modified signals step further comprises:
providing predefined parameters that are used to provide modified event timing signals to operate an I.S. machine; and
providing the modified signals to operate the I.S. machine in response to the predefined parameters, the wall thickness output signals, and the estimated temperature signals, and providing unmodified signals to operate the I.S. machine in the absence of the wall thickness output signals and the estimated temperature signals.

23. A method as defined in claim 13, wherein the generating estimated temperature signals step comprises iteratively solving the equation $$I = C_3 \int_{\lambda_1}^{\lambda_2} \frac{(1 - e^{-k_\lambda x} - r_\lambda) 2\pi c}{\lambda^4 (e^{c_2/\lambda T} - 1)} d\lambda$$

wherein I is the intensity output signal from the thermal imaging measurement device, x is the wall thickness output signal, and T the estimated temperature signal.

* * * * *